US009483773B2

(12) United States Patent
Sorensen et al.

(10) Patent No.: US 9,483,773 B2
(45) Date of Patent: *Nov. 1, 2016

(54) POINT OF VIEW SHOPPER CAMERA SYSTEM WITH ORIENTATION SENSOR

(71) Applicant: Shopper Scientist, LLC, Corbett, OR (US)

(72) Inventors: Herb Sorensen, Troutdale, OR (US); Marcus Hannon Geroux, Gladstone, OR (US); David Albers, Gresham, OR (US)

(73) Assignee: Shopper Scientist, LLC, Corbett, OR (US)

( * ) Notice: Subject to any disclaimer, the term of this patent is extended or adjusted under 35 U.S.C. 154(b) by 310 days.

This patent is subject to a terminal disclaimer.

(21) Appl. No.: 14/195,646

(22) Filed: Mar. 3, 2014

(65) Prior Publication Data

US 2014/0176723 A1 Jun. 26, 2014

Related U.S. Application Data

(63) Continuation of application No. 12/430,002, filed on Apr. 24, 2009, now Pat. No. 8,666,790.

(60) Provisional application No. 61/048,105, filed on Apr. 25, 2008.

(51) Int. Cl.
*G06Q 30/02* (2012.01)
*A61B 5/16* (2006.01)

(52) U.S. Cl.
CPC ............ *G06Q 30/0201* (2013.01); *A61B 5/16* (2013.01); *G06Q 30/02* (2013.01)

(58) Field of Classification Search
None
See application file for complete search history.

(56) References Cited

U.S. PATENT DOCUMENTS

| | | | |
|---|---|---|---|
| 6,904,408 B1 | 6/2005 | McCarthy et al. | |
| 8,666,790 B2 * | 3/2014 | Sorensen | G06Q 30/02 705/7.11 |
| 2004/0061831 A1 * | 4/2004 | Aughey | A61B 3/113 351/209 |
| 2004/0111454 A1 * | 6/2004 | Sorensen | G06Q 30/0201 708/200 |
| 2006/0010028 A1 | 1/2006 | Sorensen | |
| 2007/0185756 A1 | 8/2007 | Ahn | |
| 2008/0043013 A1 | 2/2008 | Gruttadauria et al. | |

(Continued)

OTHER PUBLICATIONS

ISA USPTO, International Search Report of PCT/US09/41721, Jun. 11, 2009, WIPO, 4 pages.

(Continued)

*Primary Examiner* — Paul Danneman
(74) *Attorney, Agent, or Firm* — Alleman Hall McCoy Rusell & Tuttle LLP

(57) ABSTRACT

A point of view shopper camera system is provided to generate and analyze shoppers' view data. The point of view shopper camera system may comprise a head device including an eye camera and a head orientation sensor, a position tracking sensor to identify a shopper's position, and an analysis computing device. The eye camera may be configured to be mounted to the head of the shopper, and to capture a still or moving image of the field of view of the shopper. The analysis computing device may be configured to receive the captured image data from the eye camera, head orientation data from the head orientation sensor, and the shopper's position data from the position tracking sensor, and determine an estimated field of view of the shopper during a trip in a shopping environment.

20 Claims, 3 Drawing Sheets

(56) References Cited

U.S. PATENT DOCUMENTS

2008/0065468 A1* 3/2008 Berg ............... G06Q 30/02
705/7.32
2008/0285805 A1* 11/2008 Luinge ............. G06F 3/011
382/107

OTHER PUBLICATIONS

Glenstrup, Arne John et al., "Eye Controlled Media: Present and Future State", University of Copenhagen, Jun. 1, 1995, 17 pages.

* cited by examiner

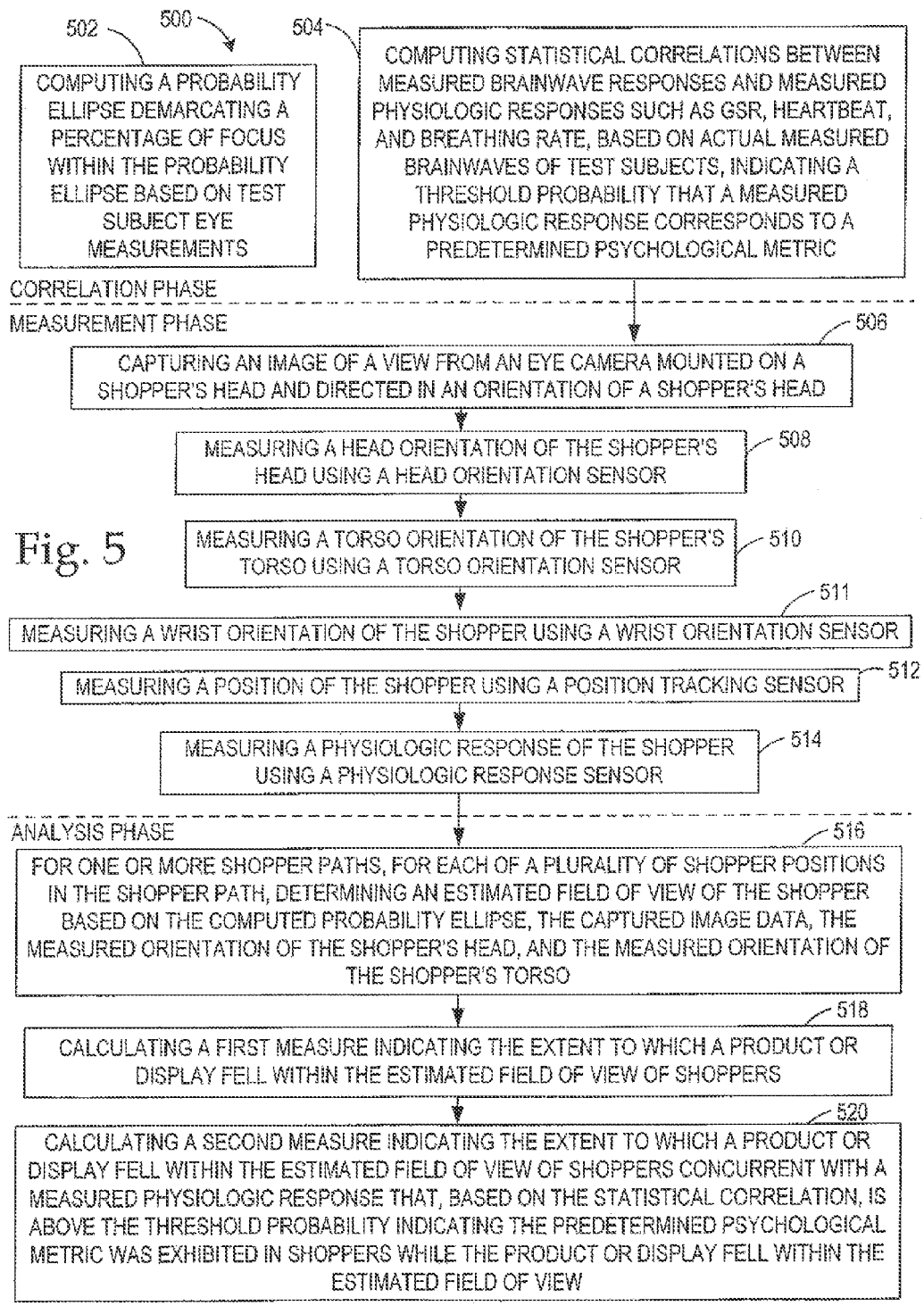

POINT OF VIEW SHOPPER CAMERA SYSTEM WITH ORIENTATION SENSOR

CROSS-REFERENCE TO RELATED APPLICATION

This application is a continuation of U.S. patent application Ser. No. 12/430,002, filed Apr. 24, 2009, entitled "Point of View Shopper Camera System with Orientation Sensor," which claims the benefit under 35 U.S.C. 119(e) of U.S. Provisional Patent Application No. 61/048,105, filed Apr. 25, 2008, entitled "Point of View Shopper Camera with Shopper Position Tracking Device and Shopper Orientation Device," the entirety of both of which are incorporated herein by reference for all purposes.

TECHNICAL FIELD

The present invention relates generally to systems and methods to analyze shopper behaviors, and more particularly to a point of view shopper camera system with a position tracking sensor and orientation sensors to determine an estimated field of view of a shopper.

BACKGROUND

In shopping research, it may be desirable to determine what a shopper is looking at or feeling during a shopping trip. However, obtaining such information with current technologies is problematic. Cameras exist that can measure actual eye movements of subjects, however these cameras are expensive and require skilled labor to operate, and thus do not scale well for large scale studies. Further, brainwave sensors exist that can be used to measure brain activity of a subject, but these brainwave sensors are also expensive thus do not scale well for large scale studies. As a result, very little reliable data exists on what shoppers see and feel during their shopping trips.

SUMMARY OF THE INVENTION

Point of view shopper camera systems and methods are provided to address the above discussed issues. The point of view shopper camera system may comprise a head device including an eye camera and a head orientation sensor, a position tracking sensor to identify a shopper's position, and an analysis computing device. The eye camera may be configured to be mounted to the head of the shopper, and to capture a still or moving image of the field of view of the shopper. The analysis computing device may be configured to receive the captured image data from the eye camera, head orientation data from the head orientation sensor, and the shopper's position data from the position tracking sensor, and determine an estimated field of view of the shopper during a trip in a shopping environment. A torso orientation sensor may also be provided, and the estimated field of view may further be based on torso orientation data received from the torso orientation sensor.

The method may include in a correlation phase, computing a probability ellipse demarcating a percentage of focus within the probability ellipse based on test subject eye measurements. The method may further include, in a measurement phase, capturing an image of a view from an eye camera mounted on a shopper's head and directed in an orientation of a shopper's head, measuring a head orientation of the shopper's head using a head orientation sensor, measuring a position of the shopper using a position tracking sensor. The method may further include, in an analysis phase, for one or more shopper paths, for each of a plurality of shopper positions in the shopper path, determining an estimated field of view of the shopper based on the computed probability ellipse, the captured image data, and the measured orientation of the shopper's head.

BRIEF DESCRIPTION OF THE DRAWINGS

FIG. 5 is a flowchart of an example method for determining an estimated field of view of a shopper in a shopping environment.

DETAILED DESCRIPTION OF THE PREFERRED EMBODIMENTS

An eye camera worn by a shopper can be used to capture a shopper's field of view. With an assumption that the eye camera sees what the shopper sees, the shopper's view, which may be said to include a line of sight and a surrounding field of view, can be estimated. When information from the eye camera is combined with the physical location of the shopper, the shopper's view data can be used to analyze the shopper's behaviors during a trip to a shopping environment, such as a store. The shopper's view from the eye camera can be estimated more accurately with information on the movement of the shopper's head or torso. Such information can be obtained from head or torso orientation sensors incorporated into a point of view shopper camera system. Further, the point of view shopper camera system can be configured to provide the shopper's position data by incorporating a shopper position tracking sensor into the system to track the shopper's positions at corresponding camera images and head or torso orientation sensor measurements.

Figure 1:
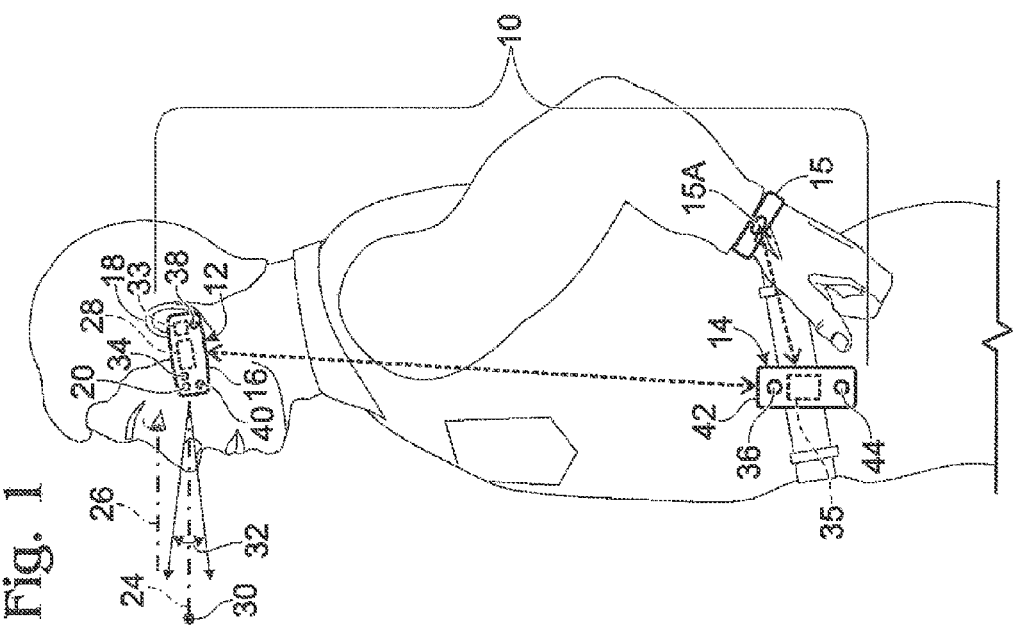
FIG. 1 shows an exemplary embodiment of a point of view shopper camera system to generate and analyze shopper view data.

FIG. 1 shows an exemplary embodiment of a point of view shopper camera system 10 to generate and analyze a shopper view data. The point of view shopper camera system 10 may be worn by shoppers recruited for studying shoppers' behaviors. The term "shopper" and "user" will be used interchangeably in the present application. As shown in FIG. 1, the point of view shopper camera system 10 may include a head device 12 and a torso device 14, which can communicate with each other and/or with a remote analysis computing device through one or more wired or wireless connections and corresponding communications interfaces on each device. In the depicted embodiment, head device 12 includes a body 16 to house various components and a fixator 18 that attaches head device 12 to the head of a shopper.

Head device 12 may include an eye camera 20 mounted in body 16 of the head device. It should be appreciated that eye camera 20 can be any suitable image capture device that fits in the body 16 and can capture the shopper's view as the shopper travels in the store, such as a small video camera or still image camera. Further, it should be appreciated that the eye camera may be positioned at any location on the shopper's head that may follow the line of sight of the shopper, as if the eyes of the user were focused straight ahead.

Head device 12 is oriented with the eye camera 20 disposed in such a manner that eye camera 20 points in a direction aligned with the orientation of the user's head, and thus points in a direction of the line of sight of the shopper. In other words, a line of sight 24 of the camera is aligned and parallel with a line of sight 26 of the user drawn as if the user's eyes were focused straight ahead relative to the position of the user's head. Line of sight 24 of the camera is thus referred to as an estimated line of sight of the user. FIG. 1 also shows an estimated focal point 30 and an estimated field of view 32.

Images, such as still images and/or moving images in the form of video, are captured via the camera and sent to an analysis computing device via a transmitter 28. These images may be recorded by a recorder, such as a still image or video recorder (not shown) as the shopper view data. It should be appreciated that transmitter 28 may be disposed in a device different from head device 12. For example, transmitter 28 may be disposed in a torso device that communicates electronically with head device 12, via a wired or wireless connection.

A timer may be incorporated into head device 12 to track the timing of images as well as other measures of shoppers' behaviors described below. The time tracking allows further correlation between the measures of shoppers' behaviors, such as the image data, the head orientation data, the torso orientation data, the shopper position data, and the physiologic responses. In this way, the estimated field of view of the shoppers can be improved. Further, the correlation makes it possible to generate additional meaningful measures of the shoppers' behaviors during the trip, such as purchases later recorded at the checkout register.

Shopper view data may be analyzed by an analysis program executed by the analysis computing device. The analysis program is configured to make the assumption for analysis purposes that the shopper sees things straight forward from the eyes (i.e., along the estimated line of sight) instead of seeing things out the corners of the eyes. This assumption is generally true in most situations, especially when shoppers visit a store for shopping. Further, the assumption may be confirmed by the shopper's head or torso orientation. Thus, a camera positioned at a suitable place on the shopper's head, such as the ear as shown in FIG. 1, can effectively follow the shopper's estimated field of view as the shopper's head and body turn back and forth during a shopping trip. The eye camera positioned in this manner can capture the estimated field of view 32 of the shopper around the estimated line of sight 24, i.e., assuming the shopper is looking straight ahead, eye camera 20 can see what the shopper is most likely seeing. One example method to estimate the shopper's view will be described below in relation to FIG. 2.

Continuing with FIG. 1, head device 12 may also include a head orientation sensor 34. Head orientation sensor 34 may be any suitable sensor that can detect head movement. In one example, head orientation sensor 34 is a gyroscopic sensor. The gyroscopic sensor, which may be implemented on a gyroscopic chip, may be incorporated into a circuit in the head device. In another example, head orientation sensor 34 is an accelerometer. The accelerometer may be placed in head device 12. Head orientation sensor 34 may provide information on head movement or direction. For example, head orientation sensor 34 may determine when the user's head turns up, down, left, or right relative to a position, such as normal walking or standing position. Head orientation sensor 34 may also provide information on a position of the user's head relative to the user's torso when the head orientation is combined with information from a torso orientation sensor 36 as described below. When the information on the head movement is combined with timing information from the timer, it is possible to determine a percentage of time a user is looking up, looking down, and a time period from head turn to torso turn, which may be used as measures of the shoppers' behaviors.

Further, information on head movement may confirm or improve the estimation on line of sight or estimated field of view. In contrast to some prior systems, in which field of view was estimated to be centered along a direction of travel of the shopper, according to embodiments of the present invention, the head orientation sensor 34 and torso orientation sensor 36 may be used to estimate the shopper's field of view based on a detected head orientation relative to a detected torso orientation. These measures may be used to determine an estimated field of view that is independent of the direction of travel, enabling a more accurate estimated field of view when the shopper is walking one direction but looking another direction. Thus, an accuracy of the estimated line of sight or estimated field of view may be improved.

Head device 12 may also include a galvanic skin response (GSR) sensor 38. Galvanic skin response sensor 38 may be disposed in a position in head device 12 such that GSR sensor 38 contacts skin to generate a physiologic response of the shopper to a particular setting. Thus, the physiologic response may be analyzed with a corresponding shopper's view to determine the shopper's response to certain images or displays in the store. In this way, the point of view shopper camera system of the present invention can provide measures of the shopper's physiologic response to a particular shopping display, such as advertising, aisle display, products, etc. It should be appreciated that other suitable physiologic measures may be sensed by sensors incorporated into head device 12 as an alternative or in addition to GSR. For example, sensors may be provided to measure physiologic responses such as heartbeat and breathing rate of the shopper. Further, it should be appreciated that the physiologic sensors may be disposed in other suitable locations on a shopper's head or torso instead of incorporation into head device 12.

Head device 12 may also include a position tracking sensor 40. In addition or in the alternative, the torso device 14 may include the position tracking sensor 40. In one example, position tracking sensor 40 is a radio frequency identification (RFID) reader. The RFID reader is configured to read RFID signals. In some shopping environments, such as a retail store, a passive RFID (not powered) is incorporated in display tags throughout the store. As a shopper travels in the store, the RFID reader can accurately track the shopper's path. Thus, the shopper's position or path data can be accurately overlaid onto the shopper's view data, head orientation, torso orientation data, and physiologic data, such that a shopper's estimated field of view, measured head orientation, measured torso orientation, and measured physiologic responses are determined for each position along the shopper's path. It should be appreciated that an RFID reader may be configured to read signals from semi-active or active RFID tags. Further, it should be appreciated that other suitable tracking methods or systems, such as mesh networks, may be used as an alternative to track a shopper's path.

FIG. 1 also shows that head device 12 may be attached to an ear of the shopper by a fixator 18. It will be appreciated that body 16 of the head device may also include an ear bud, configured to rest in an outer ear canal of the user. Further, it should be appreciated that the head device 12 may be positioned in any location on the shopper's head such that eye camera 20 may follow the head orientation and the estimated line of sight of the shopper. For example, head device 12 may be positioned on a pair of glasses worn by the shopper, on a headband or hat of the user, or other suitable device. Head device 12 may also include battery 33 to power the electronic components disposed therein.

FIG. 1 also shows that torso device 14 of point of view shopper camera system 10 may be worn on a waist belt of the user. Typically, torso device 14 includes a body 42 to house various components and a mount portion to attach torso device 14 to the torso of the user. Torso device 14 may include torso orientation sensor 36. Similar to head orientation sensor 34, torso orientation sensor 36 may be any suitable sensor that can detect torso movement. In one example, torso orientation sensor 36 is a gyroscopic sensor which may be implemented on a chip incorporated into a circuit in torso device 14. In another example, torso orientation sensor 36 is an accelerometer. A compass chip may be incorporated in the torso device to provide information on the orientation of the torso. Torso orientation sensor 36 may provide information on torso orientation. For example, torso orientation sensor 36 may determine when the user's torso turns left or right relative to a direction the user is facing. Torso orientation sensor 36 may also provide information on a position of the user's head relative to the user's torso when the information is combined with information from head orientation sensor 34. As described above, information for both sensors 34 and 36 can be used to determine how long it takes from head turn to torso turn.

Torso device 14 may also include a position tracking sensor 44. In one example, position tracking sensor 44 is a RFID reader to receive RFID signals as the user travels along the store so that the user's path can be accurately determined. While the point of view shopper camera system 10 is shown to include two position tracking sensors 40, 44, it should be appreciated that point of view shopper camera system 10 may include only one position tracking sensor. The position tracking sensor may be included either in head device 12 or torso device 14.

Torso device 12 may also include battery 35 to power the electronic components disposed therein.

FIG. 1 shows that torso device 14 is attached to a belt of the user. It should be appreciated that torso device 14 may be disposed in any other suitable position. For example, torso device 14 may be disposed in a pocket of the user or any position that is suitable to determine the torso orientation by the orientation sensor.

Figure 2:
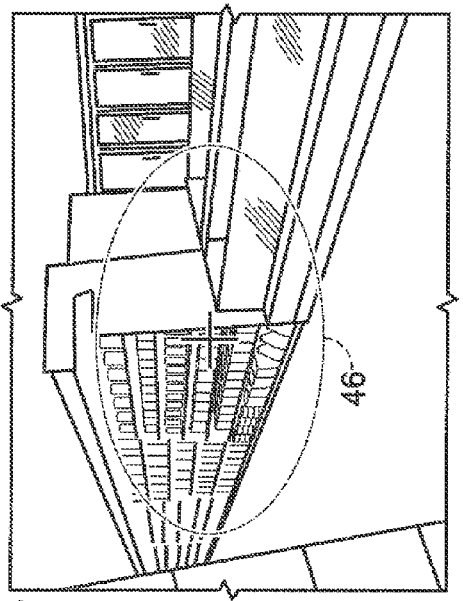
FIG. 2 illustrates an example field of view captured by the point of view shopper camera system in FIG. 1.

FIG. 1 also illustrates that the system 10 may include one or a pair of wrist devices 15 worn on the wrists of the shopper. The wrist devices 15 may include wrist orientation sensors 17 configured to generate wrist orientation data 19, as schematically illustrated in FIG. 2. The wrist sensors 17 may be gyroscopic sensors or accelerometers that are configured to measure an orientation of a user's wrist to generate the wrist orientation data 19. Wrist orientation data 19 may be transmitted from the wrist device 15 to the torso device, head device, and/or remote computer via a communication interface such as a transmitter 15A. When combined with the torso orientation data and head orientation data gathered by the system 10, the wrist orientation data can provide a fuller picture of a shopper's body position, including left and/or right arm extension, at particular positions along a shopping path. This may be useful, for example, to determine when a shopper reaches to pick up a product, for example.

Turning to FIG. 2, FIG. 2 illustrates an example field of view captured by the point of view shopper camera system 10 in FIG. 1. FIG. 2 shows a view captured by an eye camera in a retail store and a probability ellipse 46 with a center indicated by a "+" symbol, which represents a probable focus point of the line of focus of the camera. The probability ellipse may demarcate the percentage of focus of the view. In the depicted example, the probability ellipse indicates that 50% of the time a user's actual line of sight will fall within the ellipse in the field of view. Thus, there is a 50% chance that the user's actual line of sight will fall outside the ellipse. This probability ellipse may be constructed based on data collected in a correlation phase by tracking actual eye movements of actual shoppers. It should be appreciated that any suitable percentage of focus of view may be used to define the probability ellipse, and thus the size of the probability ellipse may relatively expand and contract, as desired. In another embodiment, for example, 70% or 40% probability ellipses may alternatively be used. An average focal point for all shoppers may be estimated to be the center of the ellipse as indicated by the "+" symbol. The exact location of the average focal point within the ellipse may also be determined through statistical analysis of actual eye movements of shoppers, in the correlation phase.

The above example illustrates a method to estimate the average focal point and/or probable field of focus of the shopper by using the camera data solely. As described above, the estimation may be improved because the shoppers' view can be confirmed with information on the shopper's head position and/or torso position. For example, whether the image data captured by the eye camera represent the shoppers' actual views may be identified by comparing the image data, such as average focal point and the probable field of focus with the head orientation data, torso orientation data and/or shopper position data. Because the average focal point or the probable field of focus is derived from the actual images captured by a camera that rotates with the shopper's head position, and the actual head position corresponding to the images, the shopper view data obtained from the eye camera are believed to be comparable in reliability to the data obtained from the conventional video device that measures the actual focal point by detecting the actual eye movement.

The above system utilizing a probability ellipse allows shopping behavior to be analyzed in a simple and cost effective manner by using a low-cost camera as the image capture device.

Figure 3:
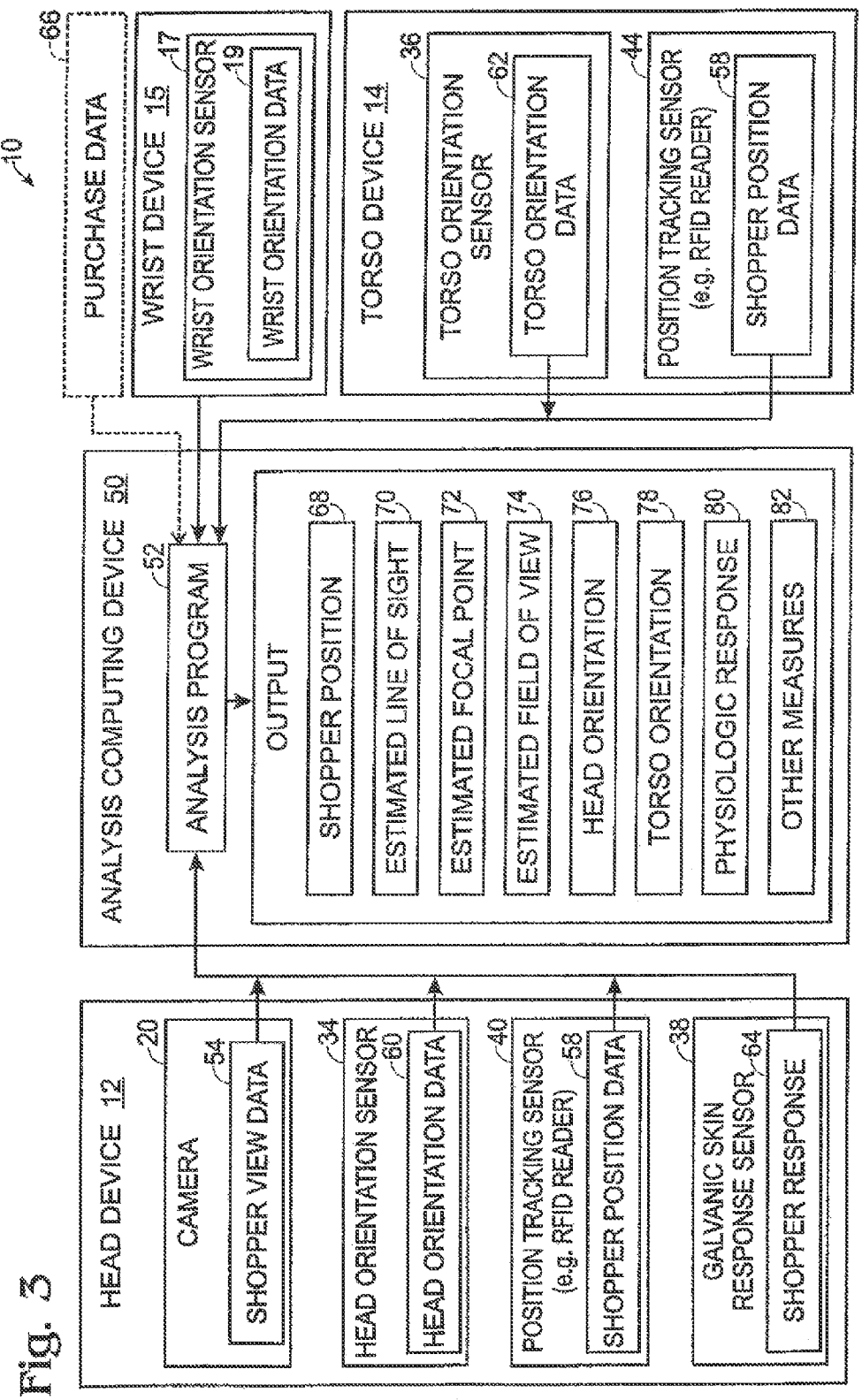
FIG. 3 shows a schematic diagram, illustrating software and hardware components of the point of view shopper camera system of FIG. 1.

FIG. 3 is a schematic diagram illustrating the point of view shopper camera system 10 of FIG. 1, further including an analysis computing device 50. It will be appreciated that analysis computing device 50 may be incorporated in head device 12 or torso device 14, or may be a computing device that is remotely connected by a communications link. The analysis computing device 50 includes a processor configured to execute an analysis program using portions of associated computer memory. The analysis computing device 50 is configured to analyze data from the point of view shopper camera system 10. As shown in FIG. 3, an analysis program 52 receives input data from head device 12, torso device 14, and wrist devices 15. The input data may include shopper view data 54, which is image data received from transmitter 28 of the eye camera 20 and recorded in image/video recorder, as well as head orientation data 60 from head orientation sensor 34, shopper position data 58 from position tracking sensor 40, and shopper physiologic response data 64 from GSR sensor 38, a heartbeat sensor or a breathing rate sensor. The input data may further include torso orientation data 62 from torso orientation sensor 36 and shopper position data 58 from RFID reader 44 disposed in torso device 14. The input data may further include wrist orientation data 19 from wrist orientation sensor 17 disposed in wrist device 15. In some embodiments, the analysis program 52 may also be configured to receive purchase data 66 from outside sources.

For each shopper, shopper view data, head orientation data, torso orientation data, wrist orientation data, and physiologic response data are overlaid with the corresponding shopper's position along a path such that various measures for the shopper's behaviors along the path can be determined by the analysis program 52. For example, output from analysis computing device 50 may include a shopper's position 68, an estimated line of sight 70, estimated focal point 72, and estimated field of view 74 at each of a plurality of specific positions along the shopper path.

The reliability of the estimated line of sight, estimated focal point, and estimated field of view of the shopper can be improved by analyzing them together with the shopper's head orientation data 76 or torso orientation data 78 and position data 68. For example, at one position along the path, the shopper's head turns to an orientation different from a previous torso orientation and the shelf display facing the head orientation is the same as the video images captured by the eye camera. Such information, along with information on the head's up or down movement, if applicable, can be used to more accurately determine an estimated field of view over prior approaches that depended on shopper's direction of travel alone. Thus, the field of view of the shopper can be accurately estimated through analysis of data from the eye camera and a plurality of sensors at a specific point.

Further, the output of the analysis computing device 50 may include data indicating one or more physiologic responses 80. Data for physiologic responses 80 such as GSR, heartbeat, and breathing rate, for example, may be assigned to values to describe the shopper's response to a particular view, either qualitatively or quantitatively.

Furthermore, other measures 82 may be developed to describe the shopper's behaviors. For example, the additional measures may include percentage of time that the shopper looks up and looks down, the time period it takes from head turn to body turn, section of display shelf the shopper is looking at, etc. Further, the analysis program may be configured to calculate other measures 82 that are based on wrist orientation data. For example, such an example measure may be a percentage of shopper trips during which a product is within an estimated field of view of a shopper and concurrently an arm extension is indicated by the wrist orientation data in the direction of a particular product.

In this way, the point of view shopper camera system can generate measures for shoppers' behaviors. Specifically, quantitative measures or metrics can be defined and generated to describe the shoppers' behaviors or shopping events.

Figure 4:
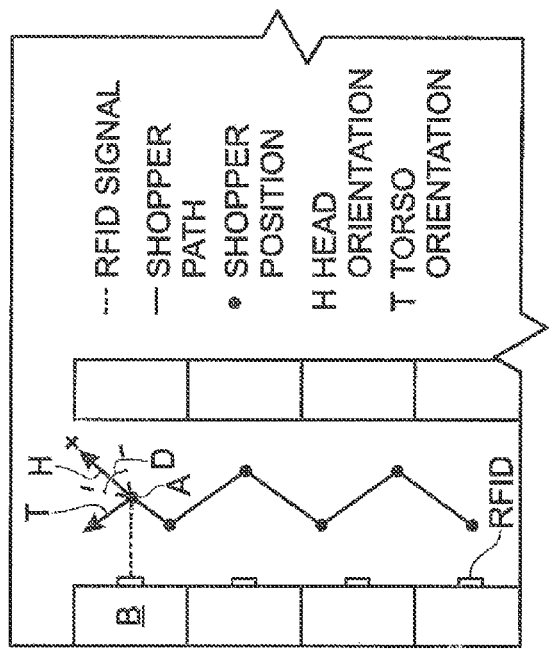
FIG. 4 shows a schematic map generated from the point of view shopper camera system of FIG. 1, as an example of output from the system.

One example output generated based on data from a point of view shopper camera system is illustrated in FIG. 4. FIG. 4 shows a schematic map generated from the point of view shopper camera system, illustrating an example output from the system. The shopper's physical positions are represented by dots and the shopper's path is represented by a solid line. An estimated point of focus is represented by the symbol "+". An estimated field of view is illustrated at D, and typically is computed to the scale of the probability ellipse described above. A head orientation at position A is indicated by an arrow H and a torso orientation at position A is indicated by an arrow T. FIG. 4 shows that the shopper's head turns at an angle relative to the torso and the head orientation H is aligned with estimated point of focus, indicated by a plus sign "+".

FIG. 4 also shows a RFID B from a RFID network in a store. Position A is determined based on signals received from RFID B. Thus, the shopper's traveling path can be overlaid or matched with measures of shopper behaviors during travel in the store, as described above. Alternatively, other path tracking technologies may be employed.

The eye camera tracking and analysis system can provide meaningful information on a shopper's behaviors. For example, the estimated points of focus may indicate the shopper's interest and attention to displays of the shopping environment. Such information is useful for media rating companies such as advertising companies regarding their placement of advertisement. Further, the eye camera system can create metrics to measure various shoppers' behaviors or shopping events. For example, for a given product position in a retail environment, the eye camera shopper view data may be used to compute an EYESHARE® measurement representing the number of shopper trips on which, and/or the total amount of time during which, the product is within the estimated field of view (e.g., within the probability ellipse described above) for a population of shoppers. For example, the shopper view data from the eye camera may be used in combination with shopper path data to estimate this measurement. Suitable methods for computing such measurements are disclosed in U.S. Pat. No. 7,006,982, entitled PURCHASE SELECTION BEHAVIOR ANALYSIS SYSTEM AND METHOD, issued Feb. 28, 2006, the entire disclosure of which is herein incorporated by reference, and U.S. patent application Ser. No. 10/667,213, entitled SHOPPING ENVIRONMENT ANALYSIS SYSTEM AND METHOD WITH NORMALIZATION, filed Sep. 19, 2003, the entire disclosure of which is also incorporated by reference.

Research has been conducted recently which attempts to measure brainwaves of subjects to determine their reactions to certain products and advertising. Brainwave measurements have been found to correlate to attention levels, emotional engagement, and other psychological metrics, which can be used to evaluate the effectiveness of products and advertising. However, as discussed above, measuring brainwaves is an expensive and time consuming process, and thus cannot be effectively scaled to large study populations shopping in actual retail environments. According to embodiments of the present invention, test data may be generated by computing statistical correlations between measured brainwave responses and measured physiologic responses such as GSR, heartbeat, and breathing rate, based on actual measured brainwaves of test subjects. Using the statistical correlations in the test data, the present system may estimate a large population of shoppers' brainwave responses to one or more shopping displays in a retail environment, based on physiologic responses (e.g., GSR, heart beat, breathing rate) that are measured when the displays fall within the shopper's estimated field of view while traveling along shopper paths in the retail environment. For example, the analysis program may determine that within a threshold probability (e.g. a 75% likelihood), a threshold percentage of shoppers (e.g., 66%) exhibited physiologic responses (e.g., GSR, heartbeat, breathing rate) that statistically correlated to a predetermined psychological metric (e.g., positive or negative emotional attachment, low, medium, or high attention levels, etc.), when a shopping display (e.g., advertisement, product, display, etc.) is determined to be within the shoppers' estimated field of view.

The point of view shopper camera system described herein has various potential advantages. Because the eye camera device can be based on inexpensive camera technology, the cost of the eye camera device can be significantly low compared with a professional quality video camera. Further, the point of view shopper camera system automatically integrates shopper's view data with shopper's position or path data. Thus, the cost associated with mapping the shoppers' paths with shoppers' view data from the eye camera by technicians or in-person auditors can be eliminated. Furthermore, the point of view shopper camera system can provide additional quantitative measures or metrics to describe the shopper's behaviors or shopping events through various sensors built-into the system.

It will be appreciated that the point of view shopper camera system can be used in combination with other shopping-related systems to consolidate or refine data obtained from the point of view shopper camera system and provide additional mechanisms to study the shopper's behaviors. For example, data of a shopper's position and line of sight of a trip in a store can be projected into a virtual store with high resolution digital images of the displays in the store. The virtual store may be created by using three dimensional visualization software, such as is used in gaming software. Based on tracking data of the shopper's position, an image of what a shopper is seeing from camera can be matched with a computed view from the virtual store by displaying the camera's image and computed view in parallel. In this way, the virtual store system can be used as a quality measure of the data generated from the point of view shopper camera system. Further, the computed view may supplement the camera data by providing more details of store display. Thus, the combination of two systems may provide accurate and meaningful data to study the shoppers' behaviors.

Further, it will be appreciated that computed models of shopping may be possible by using reality-based measures of the shopper's behavior generated by the point of view shopper camera system. For example, a virtual reality shopping trip can be created using a virtual store as a component. The computed models of shopping (e.g., shopping of an intelligent agent) can be created based on the reality-based measures. Since the computed models are based on the reality measures, the virtual reality shopping trips are validated by real trips. Thus, the shopper's behavior can be analyzed in a comprehensive and accurate manner. In one example system, several images from real-life data, modeled data, or a combination of these data types may be displayed simultaneously. For example, an image of a real-life measure, a computed vision based on a real-life measure, a virtual reality dictated by an intelligent agent model, or a virtual reality trip taken by a real shopper may be displayed in parallel to enable detailed analysis of the shopper's behavior.

Turning now to FIG. 5, an embodiment of a method is illustrated at 500, to generate and analyze a shopper view data during a trip in a shopping environment. It will be appreciated that method 500 may be executed using the hardware and software components described above, or other suitable components. Method 500 may include, at 502, in a correlation phase, computing a probability ellipse demarcating a percentage of focus within the probability ellipse based on test subject eye measurements. At 504, the method may further include, in the correlation phase, computing statistical correlations between measured brainwave responses and measured physiologic responses including galvanic skin response, heartbeat, and or breathing rate, based on actual measured brainwaves of test subjects, indicating a threshold probability that a measured physiologic response corresponds to a predetermined psychological metric.

Following the correlation phase, the method 500 may enter into a measurement phase encompassing steps 506-514, in which data is gathered from one or more shoppers shopping in a store or other retail environment. At 506, the method may include, capturing an image of a view from an eye camera mounted on a shopper's head and directed in an orientation of a shopper's head, as discussed above. At 508, the method may include measuring a head orientation of the shopper's head using a head orientation sensor. At 510, the method may include measuring a torso orientation of the shopper's torso using a torso orientation sensor. At 511, the method may also include measuring a wrist orientation of one or more wrists of a shopper using a wrist orientation sensor of a wrist device worn by the shopper. At 512, the method may include measuring a position of the shopper using a position tracking sensor. At 514, the method may include, measuring a physiologic response of the shopper using a physiologic response sensor. The physiologic response may be a galvanic skin response, heartbeat, breathing rate, or other physiologic response, as discussed above.

Following the measurement phase, the method 500 may enter an analysis phase, encompassing steps 516-520, during which data gathered from shoppers is analyzed. In the analysis phase, the method 500 may include at 516, for one or more shopper paths, for each of a plurality of shopper positions in the shopper path, determining an estimated field of view of the shopper based on the computed probability ellipse, the captured image data, the measured orientation of the shoppers head, and the measured orientation of the shopper's torso. At 518, the method may further include calculating a first measure indicating the extent to which a product or display fell within the estimated field of view for the one or more shopper paths. At 520, the method may include calculating a second measure indicating the extent to which a product or display fell within the estimated field of view of shoppers, concurrent with a measured physiologic response that, based on the statistical correlation, is above the threshold probability indicating that the predetermined psychological metric was exhibited in shoppers while the product or display fell within the estimated view. It will be appreciated that the method may further include calculating other measures that are based on the measured wrist orientation data, in addition to the various other data types discussed above. For example, a measure that indicates the percentage of shopper trips during which a shopper extended an arm in the direction of a product while the product is within a shopper's estimated field of view may be computed.

The above described method may be used to efficiently obtain an estimated shopper field of view for various positions along a shopper path, and determine measures indicating whether particular products fell within the field of view, and/or whether psychological metrics were exhibited by shoppers such products fell within the field of view. The method avoids the necessity in prior approaches of measuring actual eye movements or brainwaves of individual shoppers, thereby saving time and money as compared to such approaches.

Although the above example embodiments have been described for use in a shopping environments such as a retail store, it should be appreciated that the method and system can be applied to various other applications in order to categorize specific events and behaviors.

It should be understood that the embodiments herein are illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A method to generate and analyze shopper view data in a shopping environment, comprising:
    in a correlation phase, computing a probable field of focus demarcating a percentage of focus within the probable field of focus in a field of view of an eye camera based on test subject eye measurements;
    in a measurement phase, capturing an image of a view from the eye camera mounted on a shopper's head and directed in an orientation of the shopper's head;
    measuring a head orientation of the shopper's head using a head orientation sensor;
    measuring a position of the shopper using a position tracking sensor; and
    in an analysis phase, for one or more shopper paths, for each of a plurality of shopper positions in the shopper path, determining an estimated field of view of the shopper based on the computed probable field of focus, captured image data, and the measured orientation of the shopper's head.

2. The method of claim 1, further comprising, in the analysis phase, calculating a first measure indicating the extent to which a product or display fell within the estimated field of view for the one or more shopper paths.

3. The method of claim 2, further comprising:
    in the correlation phase, computing statistical correlations between measured brainwave responses and measured physiologic responses based on actual measured brainwaves of test subjects, indicating a threshold probability that a measured physiologic response corresponds to a predetermined psychological metric.

4. The method of claim 3, further comprising:
    in the measurement phase, measuring a physiologic response of the shopper using a physiologic response sensor.

5. The method of claim 4, further comprising:
    in the analysis phase, calculating a second measure indicating the extent to which a product or display fell within the estimated field of view of the shopper, concurrent with a measured physiologic response that, based on the statistical correlation, is above the threshold probability indicating that the predetermined psychological metric was exhibited in shoppers while the product or display fell within the estimated field of view.

6. The method of claim 5, wherein the physiologic response is one or more of galvanic skin response, heartbeat, and/or breathing rate.

7. The method of claim 1, further comprising:
    measuring a torso orientation of the shopper's torso using a torso orientation sensor;
    wherein determining an estimated field of view of the shopper is further based on the measured orientation of the shopper's torso.

8. The method of claim 1, further comprising, for each of the plurality of shopper positions in the shopper path, determining an estimated line of sight and/or estimated focal point, associated with the estimated field of view.

9. A point of view shopper camera system to generate and analyze shopper view data of a shopper from a shopping trip in a shopping environment, comprising:
    a head device to be mounted to a shopper's head, including: a camera configured to point in a direction aligned with an orientation of the head of the shopper to capture image data including an image of a view that the shopper sees when eyes of the shopper focus straight ahead;
    a head orientation sensor to generate head orientation data;
    a position tracking sensor to identify shopper position and generate shopper position data; and
    a communication interface configured to transmit the captured image data, head orientation data, and shopper position data to an analysis program executed on an analysis computing device;
    wherein the analysis program is configured to determine an estimated field of view of the shopper based on the image data, including a probable field of focus demarcating a percentage of focus within the probable field of focus in a field of view of the camera based on test subject eye measurements, the head orientation data, and the shopper position data.

10. The system of claim 9, further comprising:
    a torso device to be mounted to a shopper's torso, including a torso orientation sensor to generate torso orientation data; and
    wherein the analysis program is configured to determine the estimated field of view of the shopper further based on the torso orientation data.

11. The system of claim 10, wherein the estimated field of view is determined at least in part by calculating an average focal point and the probable field of focus of the shopper using the image data and comparing the average focal point and the probable field of focus with a relative position of between the shopper's head and the shopper's torso using the head orientation data and the torso orientation data.

12. The system of claim 9, further comprising:
    a wrist device worn on a wrist of the shopper, the wrist device including a wrist orientation sensor configured to measure an orientation of the wrist to generate wrist orientation data;
    wherein the analysis program is configured to calculate a measure based on the wrist orientation data.

13. The system of claim 9, wherein the head device further comprises a physiologic response sensor configured to detect a physiologic response of the shopper and generate physiologic response data to be transmitted to the analysis program.

14. The system of claim 13, wherein the physiologic sensor includes a galvanic skin response sensor, a heartbeat sensor, or a breathing rate sensor.

15. The system of claim 14, further comprises a timer to track timing and correlate the timing with the image data, the head orientation data, the torso orientation data, the shopper position data, and the physiologic response data during the trip.

16. The system of claim 9, wherein the position tracking sensor is a radio frequency identification (RFID) reader configured to receive signals from a RFID network in the shopping environment.

17. The system of claim 9, wherein the head orientation sensor measures a movement of the shopper's head to determine whether the shopper looks up, down, left, or right.

18. A method to generate and analyze shopper view data in a shopping environment, comprising:

in a correlation phase, computing a probable field of focus of a field of view of an eye camera demarcating a percentage of focus within the probable field of focus based on test subject eye measurements;

in a measurement phase, capturing an image of a view from the eye camera mounted on a shopper's head and directed in an orientation of the shopper's head;

measuring a head orientation of the shopper's head using a head orientation sensor;

measuring a position of the shopper using a position tracking sensor;

measuring a torso orientation of the shopper's torso using a torso orientation sensor; and in an analysis phase, for one or more shopper paths, for each of a plurality of shopper positions in the shopper path, determining an estimated field of view, an estimated line of sight and/or estimated focal point of the shopper based on the computed probable field of focus, captured image data, the measured orientation of the shopper's head, and the measured orientation of the shopper's torso.

19. The method of claim 18, further comprising, in the analysis phase, calculating a first measure indicating the extent to which a product or display fell within the estimated field of view for the one or more shopper paths.

20. The method of claim 18, further comprising:

in the correlation phase, computing statistical correlations between measured brainwave responses and measured physiologic responses based on actual measured brainwaves of test subjects, indicating a threshold probability that a measured physiologic response corresponds to a predetermined psychological metric;

in the measurement phase, measuring a physiologic response of the shopper using a physiologic response sensor;

in the analysis phase, calculating a second measure indicating the extent to which a product or display fell within an estimated field of view of shoppers, concurrent with a measured physiologic response that, based on the statistical correlation, is above the threshold probability indicating that the predetermined psychological metric was exhibited in shoppers while the product or display fell within the estimated field of view; and wherein the physiologic response is one or more of galvanic skin response, heartbeat, and/or breathing rate.

* * * * *